United States Patent [19]

Steer

[11] 4,006,744
[45] Feb. 8, 1977

[54] LOCKING CANNULA MOUNT

[75] Inventor: Peter Leslie Steer, East Grinstead, England

[73] Assignee: Abbott Laboratories, North Chicago, Ill.

[22] Filed: June 23, 1975

[21] Appl. No.: 589,278

[30] Foreign Application Priority Data

June 24, 1974 United Kingdom ............ 27854/74

[52] U.S. Cl. .................... 128/214 R; 128/214.4; 128/348
[51] Int. Cl.² ........................................ A61M 5/00
[58] Field of Search ......... 128/214 R, 214.2, 214.4, 128/221, 348, DIG. 16

[56] References Cited

UNITED STATES PATENTS

| | | | |
|---|---|---|---|
| 3,537,451 | 11/1970 | Beck et al. | 128/214.4 |
| 3,538,915 | 11/1970 | Frampton et al. | 128/214 R |
| 3,589,361 | 6/1971 | Loper et al. | 128/214.4 |
| 3,592,192 | 7/1971 | Harautuneian | 128/214.4 |
| 3,834,380 | 9/1974 | Boyd | 128/133 |

Primary Examiner—Dalton L. Truluck
Attorney, Agent, or Firm—Robert L. Niblack; Neil E. Hamilton

[57] ABSTRACT

A device for securing a length of cannula tubing to facilitate the introduction of fluids into the tubing wherein a sleeve of flexible tubing is disposed between an entry passage for the cannula tubing and an opposing entry passage for communication with a source of fluid. Hinged jaw or wing members compress the flexible sleeve against the cannula tubing when it is placed therein thereby providing a fluid-tight and secure arrangement. In a preferred embodiment, a releasable snap-fit means is disposed on the wing members and tabular flange-like projections extend from the wings or jaws to facilitate the opening and closing of the jaw members.

10 Claims, 5 Drawing Figures

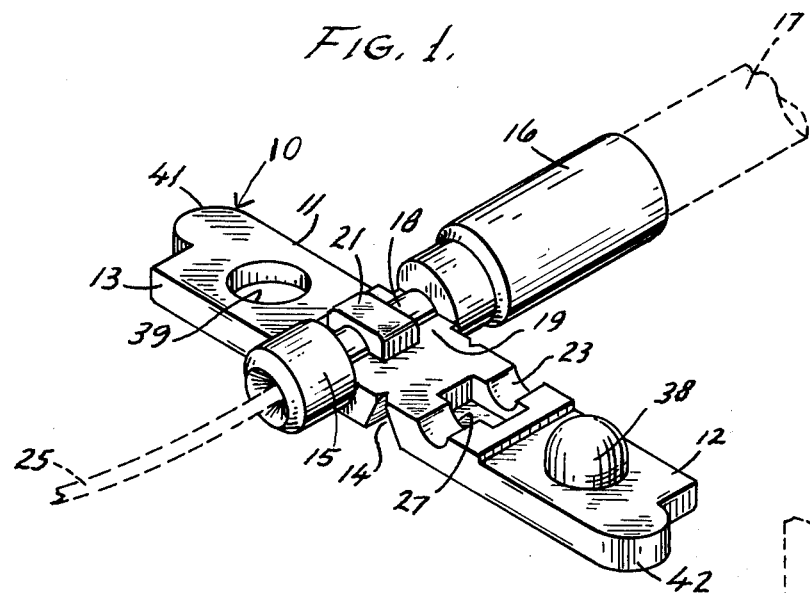
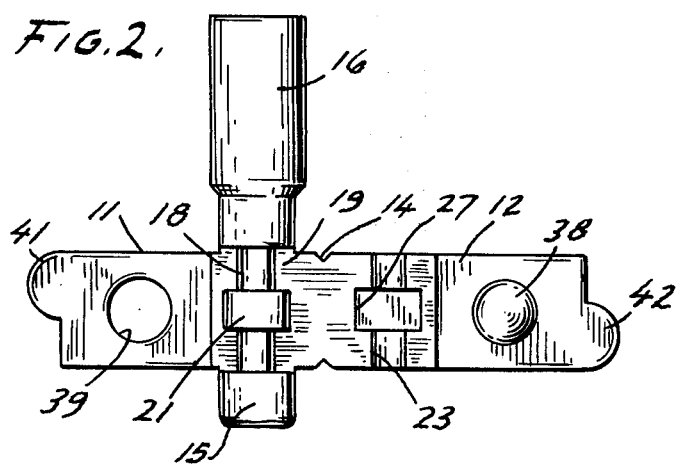
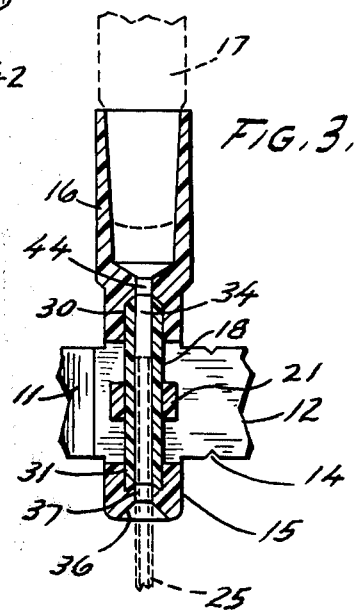
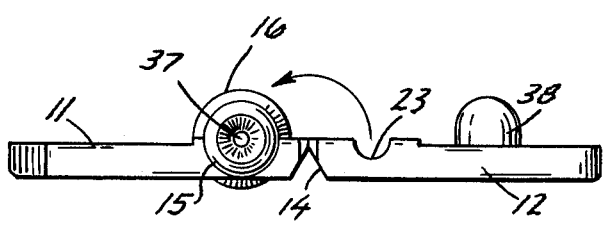
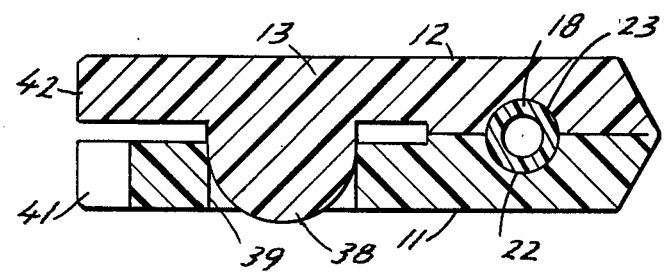

LOCKING CANNULA MOUNT

BACKGROUND OF THE INVENTION

This invention relates to devices for joining cannula or other fine bore tubes to fittings such as luer lock fittings.

In surgery it is often necessary to fit a device such as a luer mount to a cannula. For example, in the epidural cannulization of women for painless childbirth, a needle is inserted into the epidural space of the patient and a cannula is passed through the needle into the patient. The needle can then be removed and a mount fitted, but this is a difficult procedure because it is not easy for a person wearing rubber gloves to fit a fine needle end into a tube. Alternatively, the needle can be left on the cannula and then taped down onto the patient, but there is then a risk that the needle will cut the tube. An advantage of the invention is to provide a way of avoiding these problems, but it should be understood that the use of the device of the present invention is not restricted to use for epidural cannulization of a patient.

Holders for tubular items of the type concerned with in this invention can be found in U.S. Pat. Nos. 3,538,915; 3,574,306; 3,589,361; 3,592,192; 3,834,380. In U.S. Pat. Nos. 3,538,915 and 3,574,306, devices are disclosed for inseparably securing an infusion needle to a wing-type holder. A holder for cannula tubing is illustrated in U.S. Pat. No. 3,589,361 and in U.S. Pat. No. 3,834,380. In U.S. Pat. No. 3,592,192, a clamping unit is indicated for securing a cannula and catheter together. However, none of these prior art devices affords a fluid-tight fitment by means of an intermediate length of flexible tubing which is compressed around the catheter tubing after being inserted therein.

SUMMARY OF THE INVENTION

According to the invention, a mount arranged to be fitted on an end of a cannula is provided with a first clamping jaw secured to the mount adjacent a cannula inlet to the mount. A cannula inlet member is secured to the jaw opposite the cannula fluid inlet of the mount. A resilient inlet sleeve or tube extends between the cannula inlet member and the cannula fluid inlet of the mount whereby an end portion of the cannula can be passed through the inlet member and the tube to the mount. A second jaw is hinged to the first jaw and can be closed onto the first jaw and onto the sleeve thereby to clamp the cannula portion in the sleeve. Means are provided for locking the two jaws together in the closed position.

In a preferred embodiment of the invention, a cannula mount, for example a luer mount, is secured at one end to a pair of clamping jaws which can be locked together to secure the device to an end portion of a cannula leading to the mount. For convenience of description, the luer mount is herein considered to be positioned above the jaws. The mount and the two jaws are preferably molded in one piece from a suitable plastic material.

BRIEF DESCRIPTION OF THE DRAWING

A better understanding of the present device will be afforded by reference to the drawing wherein:

FIG. 1 is a perspective view of the locking cannula mount with the wings or clamping jaws in an open position and having a length of cannula tubing extending from one end and the luer taper portion of a hypodermic syringe engaging the luer mount at the opposing end.

FIG. 2 is a top plan view of the unit shown in FIG. 1 without the tubing and the syringe portion.

FIG. 3 is a partial view in horizontal section of the unit illustrated in FIG. 1.

FIG. 4 is an end view of the locking cannula mount shown in FIG. 2 illustrating the movement of the one jaw or wing member over the other to effect a clamping or compressing action on the centrally disposed tubing.

FIG. 5 is a view in vertical section of the clamping jaws engaging each other with the centrally disposed flexible tubing compressed therein.

DESCRIPTION OF THE PREFERRED EMBODIMENT

Referring to FIG. 1, the locking cannula mount 10 is composed of two oppositely positioned wing or jaw members 11 & 12 which are joined by a weakened hinge portion 14. The wing members 11 and 12 form a part of a body member 13 from which extends an annular cannula inlet passage 15. Extending oppositely to the inlet passage 15 is an entry mount or compartment 16 which has a luer taper inside to accommodate a luer taper portion 17 of a hypodermic syringe. Interconnecting the inlet passage 15 and the compartment 16 is a length of flexible tubing or a sleeve 18 which is secured in an intermediate section 19 in jaw member 11 of body member 13 adjacent hinge 14.

It will be seen that sleeve 18 is secured in the wing or jaw 11 by an intermediate retaining member 21 which surrounds sleeve 18 in a semicircular manner. As will best be seen in FIG. 5, sleeve 18 is accommodated in jaw member 11 by means of semicircular groove 22. It is contacted by groove 23 in jaw 12 which has a radius of curvature slightly smaller than the outside diameter of sleeve 18 so as to effect a compressive force on it when the catheter tubing 25 is inserted therein. It will be noted that groove 23 is interrupted by a central rectangular passage 27 which will accommodate the intermediate retaining member when the jaws are in a locking position as shown in FIG. 5, and the wall surface of groove 23 will compress sleeve 18 on each side of the retaining member 21.

As best seen in FIG. 3, sleeve 18 is accommodated in enlarged passages 30 and 31 in compartment 16 and inlet passage 15. This provides a central coaxially aligned channel 34 extending between the luer taper compartment and inlet 15. It should be noted that a small diameter portion 37 is disposed in inlet passage 15 with the internal diameter being substantially the same as the internal diameter of sleeve 18. This with the conical entry port 36 having a larger diameter than sleeve 18 affords ready and quick insertion of catheter tubing 25 in sleeve 18.

It should also be noted in FIGS. 1, 2, 4 and 5 that a retentive frictional engaging means for the wings or jaws 11 and 12 is provided in the form of a knob 38 and an opening 39 into which the knob 38 will frictionally fit when the jaws are in a closed position as indicated in FIG. 5.

It will also be seen with respect to FIGS. 1 and 2 that wings 11 and 12 are provided with opposing and offsetting flanges 41 and 42 which will aid in separating the wing portions when knob 38 engages opening 39.

OPERATION

A better understanding of the locking cannula mount 10 will be had by a description of its operation. A length of catheter tubing 25 will be inserted into the epidural space of a patient in the usual manner employing a cannula. When the needle or cannula is removed, it is desired to then introduce fluid materials into the cannula. With the cannula properly positioned in the patient, the opposing end is inserted into entry 36 and inwardly into sleeve 28 a sufficient distance so that proper clamping action of the sleeve can be effected. In this regard, reference is made to FIG. 3 which shows the cannula 25 in sleeve 18. After insertion of the cannula in the sleeve member, the jaw members 11 and 12 are brought together by means of the hinge 14 with knob 38 fitting into opening 39 in a frictional manner. This causes semicircular groove 23 to engage sleeve 18 on either side of retaining member 21 thereby compressing the resilient sleeve firmly but gently around the cannula which is thereby clamped in the sleeve. Introduction of parenteral solution or fluids is easily effected by means of a luer taper syringe such as indicated at 17 which is inserted into compartment 16. A fluid-tight connection is thereby made as the cannula 25 is firmly held in sleeve 18 with sleeve 18 communicating with the inside of entry compartment 16 through small diameter portion 44. With the jaws or wings 11 and 12 interconnected, the unit is easily secured to a patient by means of adhesive tape. When it is desired to release cannula 25, all that is required is for the wing members 11 and 12 to be separated by grasping flanges 41 and 42 and forcing them in an opposing direction.

The locking cannula mount body 13 is easily molded from various resinous plastic materials and resilient sleeve 18 is fabricated from rubber or rubber-like material. Sleeve 18 can be secured in passages 30, 31, groove 22 and through retaining member 21 by means of molding. The locking cannula mount 10 is easily molded in one piece. Various configurations can be provided for the jaws 11 and 12 as well as various sizes to provide sufficient surface area for applying adhesive tape so as to secure the locking cannula mount to a patient. It will also be appreciated that while a snap-type fitment of a knob 38 and opening 39 is illustrated, other retentive retaining means could be employed such as a metal clip or a latch-type mechanism. However, as the knob and opening arrangement of this unit 10 does not require any moving parts, it is preferred.

It will thus be seen that through the present invention there is now provided a locking cannula device wherein a length of cannula tubing can be quickly inserted and clamped in a fluid-tight manner. The jaw members are easily manipulated and a large compartment is afforded for the introduction of fluids into the cannula from the opposing end. The unit is readily molded from standard plastic materials and requires no moving parts except for a hinging action.

The foregoing invention can now be practiced by those skilled in the art. Such skilled persons will know that the invention is not necessarily restricted to the particular embodiments herein. The scope of the invention is to be defined by the terms of the following claims as given meaning by the preceding description.

I claim:

1. A device for securing a length of cannula tubing to facilitate the introduction of fluids into said tubing comprising:
    a body member defining an inlet passage for said cannula tubing,
    an opposing entry passage for contact with a source of fluid and an intermediate section,
    a length of intermediate flexible tubing secured to said intermediate section and communicating with said opposing inlet and entry passages,
    said length of intermediate flexible tubing adapted to receive an end portion of said cannula tubing,
    means to secure said length of intermediate flexible tubing between said inlet and entry passages,
    said body member further defining a hinged clamping member constructed and arranged to engage said intermediate flexible tubing and to compress said intermediate tubing against said cannula tubing in a fluid tight manner,
    and means operatively associated with said body member to tentatively retain said hinged clamping member in engagement with said intermediate flexible tubing.

2. The device as defined in claim 1 wherein said entry passage to said intermediate tubing is defined by an annular entry port of larger diameter than said length of intermediate tubing communicating therewith.

3. The device as defined in claim 2 wherein said entry port for fluid is defined by a compartment defining a luer taper.

4. The device as defined in claim 1 wherein said intermediate tubing is secured in part by a groove in said body member and a permanent retaining member engaging said intermediate flexible tubing and surrounding said intermediate tubing.

5. The device as defined in claim 4 wherein said body member is defined by two wing-like members with an additional groove in one of said members, one said groove constructed and arranged to fully accommodate said retaining member and to partially accommodate said flexible tubing in a constricting manner.

6. The device as defined in claim 5 wherein said wing-like members are hinged by means of a weakened portion adjacent said intermediate flexible tubing.

7. The device as defined in claim 6 wherein said means to tentatively retain the hinged wing-like members is an integral snap fit means disposed in said wing portions.

8. The device as defined in claim 7 further including offsetting flange members extending on each wing-like member to facilitate opening and closing of said wings.

9. The device as defined in claim 8 wherein said wing-like members are fabricated from a plastic material.

10. The device as defined in claim 3 wherein entry passage and said compartment are defined by enlarged passage portions with said length of intermediate flexible tubing extending therein.

* * * * *

UNITED STATES PATENT AND TRADEMARK OFFICE
CERTIFICATE OF CORRECTION

PATENT NO. : 4,006,744
DATED : February 8, 1977
INVENTOR(S) : Peter Leslie Steer It is certified that error appears in the above-identified patent and that said Letters Patent are hereby corrected as shown below:

In Column 3, line 11, please delete the numeral 28 and substitute therefor the numeral 18.

Signed and Sealed this

Third Day of May 1977

[SEAL]

Attest:

RUTH C. MASON
Attesting Officer

C. MARSHALL DANN
Commissioner of Patents and Trademarks